(12) United States Patent
Rudberg et al.

(10) Patent No.: US 6,210,387 B1
(45) Date of Patent: Apr. 3, 2001

(54) DISPOSABLE LIQUID-ABSORBENT ARTICLE COMPRISING PRETENSIONALLY APPLIED ELASTIC MEANS

(75) Inventors: Åsa Rudberg, Göteborg; Carina Mare, Västra Frölunda, both of (SE)

(73) Assignee: SCA Hygiene Products Aktiebolag, Gothenburg (SE)

( * ) Notice: Subject to any disclaimer, the term of this patent is extended or adjusted under 35 U.S.C. 154(b) by 0 days.

(21) Appl. No.: 09/068,513

(22) PCT Filed: Nov. 14, 1996

(86) PCT No.: PCT/SE96/01469

§ 371 Date: May 12, 1998

§ 102(e) Date: May 12, 1998

(87) PCT Pub. No.: WO97/17921

PCT Pub. Date: May 22, 1997

(30) Foreign Application Priority Data

Nov. 16, 1995 (SE) .................................................. 9504076

(51) Int. Cl.[7] .............................. A61F 13/15; A61F 13/20
(52) U.S. Cl. .................... 604/385.27; 604/358; 604/378; 604/383; 604/385.01; 604/385.101; 604/385.23; 604/385.24
(58) Field of Search .............................. 604/385.1, 385.2, 604/385.01, 385.16, 385.22, 385.24, 385.27, 385.101, 358, 378, 383, 385.23

(56) References Cited

U.S. PATENT DOCUMENTS

| 3,860,003 | 1/1975 | Buell . |
| 4,050,462 | 9/1977 | Woon et al. . |
| 4,326,528 | * 4/1982 | Ryans et al. ........................ 128/287 |
| 4,770,657 | * 9/1988 | Ellis et al. ............................ 604/385 |
| 4,801,345 | 1/1989 | Dussaud et al. . |
| 5,752,946 | 5/1998 | Boberg et al. . |

FOREIGN PATENT DOCUMENTS

| 0 219 326 A2 | 4/1987 | (EP) . |
| 0 626 160 A1 | 11/1994 | (EP) . |
| 2 234 157 | 1/1991 | (GB) . |
| 2 272 708 | 5/1994 | (GB) . |
| WO 88/00010 | 1/1988 | (WO) . |
| WO 94/28844 | 12/1994 | (WO) . |
| WO 96/18366 | 6/1996 | (WO) . |

* cited by examiner

Primary Examiner—John G. Weiss
Assistant Examiner—Michele Kidwell
(74) Attorney, Agent, or Firm—Burns, Doane, Swecker & Mathis, L.L.P.

(57) ABSTRACT

The invention relates to liquid-absorbent articles, including diapers, training pants, incontinence guards, and sanitary napkins.

Characteristic for the invention is that at least one of the end portions of the absorbent body has a longitudinally tapering shape with a rounded outer edge and that an elastic means is pretensionally applied in a cover enclosing the absorbent body and extends across the article and in a curved path outside the rounded end portion of the absorbent body and equidistantly from the rounded edge. Due to its striving to contract, the elastic means in the curved path section exerts tensile forces across the elastic in a direction towards the center of curvature of the curved path section. When the article is in use, the elastic means, due to the tensile force, lifts the cover around the rounded edge of the absorbent body for formation of a leakage barrier which projects vertically above the absorbent body.

5 Claims, 3 Drawing Sheets

DISPOSABLE LIQUID-ABSORBENT ARTICLE COMPRISING PRETENSIONALLY APPLIED ELASTIC MEANS

TECHNICAL FIELD

The present invention relates to a disposable liquid-absorbent article according to the preamble of claim 1.

BACKGROUND OF THE INVENTION

Liquid-absorbent articles, for example diapers are known which are provided with elastic in order to impart shape to the article when in use. In the majority of such articles, the main purpose of the elastic is to form an erect edge which seals against the legs of the wearer. Hitherto known solutions have, however, a limited capacity in terms of the ability to locally collect and enclose larger volumes of, for example, faeces and urine.

A pair of training pants is known from for example U.S. Pat. No. 3,860,003, in which leg elastic forms an encompassing sleeve around the legs. When the article is in a folded-out condition, the elastic is completely rectilinear and extends essentially along the side of the absorbent body in order to permit the edge of the diaper to seal against the legs when in use.

U.S. Pat. No. 4,050,462 relates to a diaper with elastic, which in the levelled condition of the diaper extends rectilinearly and is intended to contract the crotch area of the diaper and increase the surface and the volume per unit of length of the absorbent body by the formation of pleats in order to obtain an enhanced absorption effect.

WO 88/00010 discloses a diaper with principally rectilinear elastic forming a V-shaped configuration. The elastic extends across the absorbent body of the diaper and demarcates a region which is deformed by the contracting action of the elastics. The extension of the elastic with rectilinear portions mainly achieves a pleating of the article as a whole as the elastic strives to reduce the total length of the article. A region enclosed between a number of rectilinear elastic portions is imparted a bowl-like shape through the contraction of the elastic portions.

U.S. Pat. No. 4,801,345 discloses a method for the manufacture of diapers. The method involves application of elastics along the crotch portion of the diaper. In this manner the elastic extends concavely outwards along the long edges of the diaper and totally to the side of the absorbent body. The purpose of the elastic is primarily to achieve a tight connection of the edge of the diaper against the leg of the wearer. A further effect will be a certain contraction and pleating of the absorbent body across the crotch portion.

EP 0,219,326 discloses a diaper with elastic which extends completely rectilinearly in a levelled condition of the diaper and totally to the side of the absorbent body. Elastic is arranged slong the outer edge of the diaper on both sides of the crotch portion and in a trimming on both sides of the absorbent body. In addition to maintaining an erect, sealing edge by means of the trimming, the elastic ensures a certain pleating and contraction of the absorbent body.

GB 2,234,157 relates to a pair of training pants with elastic which extends around the waistband of the training pants and along the edge of the crotch portion against the legs of the wearer, as well as across the crotch portion. The elastic which encompasses the legs reduces the risk of leakage, while the elastic across the crotch portion is only arranged so as to enable a rational application of continuous elastic threads. The construction and the method are especially adapted to diapers in the form of training pants.

SUMMARY OF THE INVENTION

The object of the present invention is to provide a disposable liquid-absorbent article which in use adapts a very efficient collecting shape.

Since diapers with leg elastic according to U.S. Pat. No. 3,860,003 became common during the sixties, an immense number of patent applications regarding elastic in diapers has been filed around the world.

Elastic has been applied longitudinally and/or transversally of the diaper in order to form a 3-dimensional shape or leakage barriers.

Elastic has also been applied in a curve shape along the edge portions of the cover outside the side edges of the absorbent body, which curve shape, however, has been chosen merely for better adaptation to the body shape of the user.

Thanks to the present invention, the shape of the absorbent body and the application shape of the elastic have been adapted to each other in a simple way to create a completely novel elastic effect which imparts immense advantages to the product.

Said object and the novel effect are achieved by an article in accordance with the present invention, the features of which are evident from the claim 1.

BRIEF DESCRIPTION OF THE DRAWINGS

The invention will be described in the following by means of an embodiment and with reference to the attached drawings, in which.

DETAILED DESCRIPTION OF PREFERRED EMBODIMENTS

Diapers for incontinent persons, i.e. adults suffering from incontinence, have been chosen as an embodiment.

Figure 1:
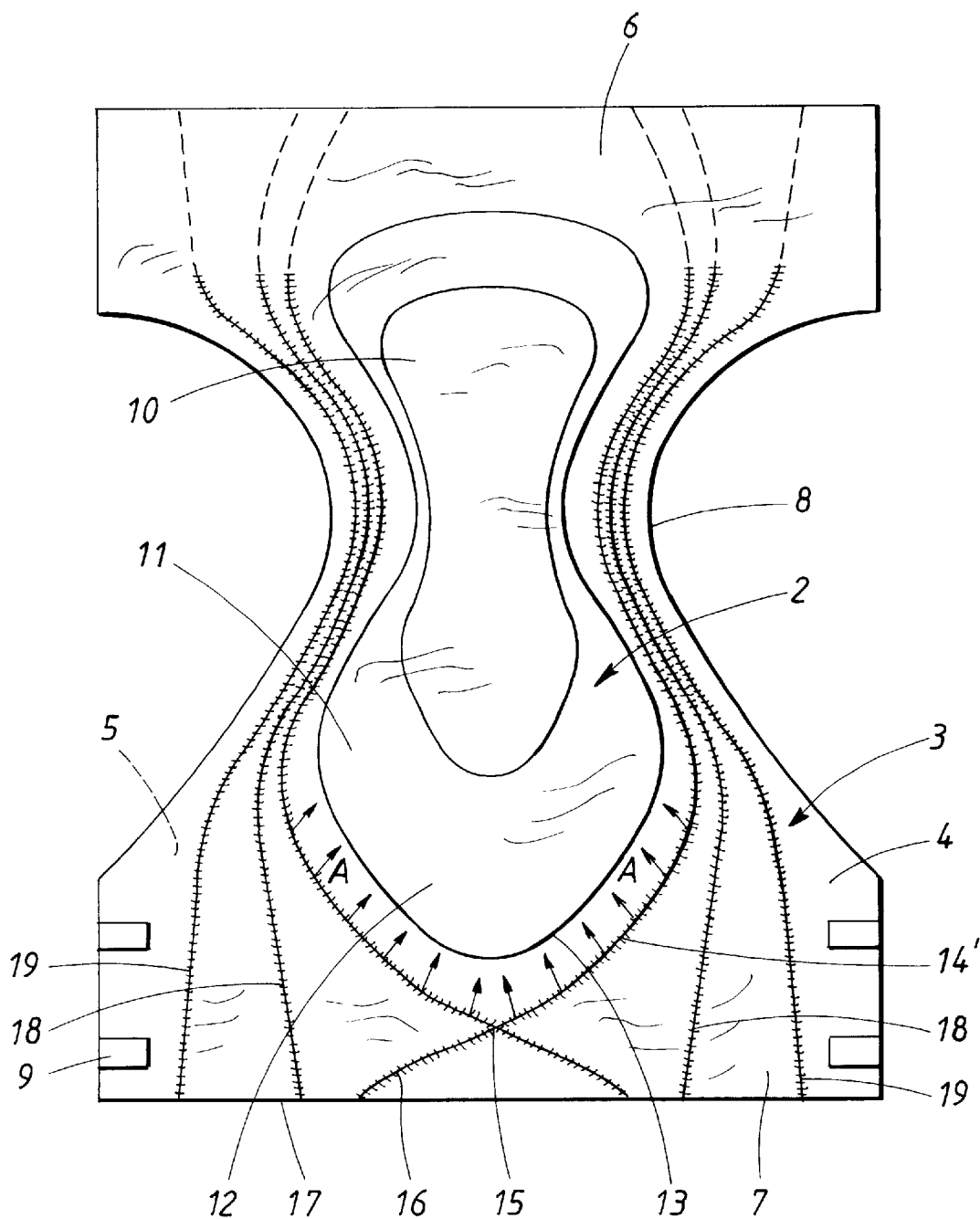
FIG. 1 is a plan view of an article according to the invention according to a first embodiment in the form of a diaper
Figure 2:
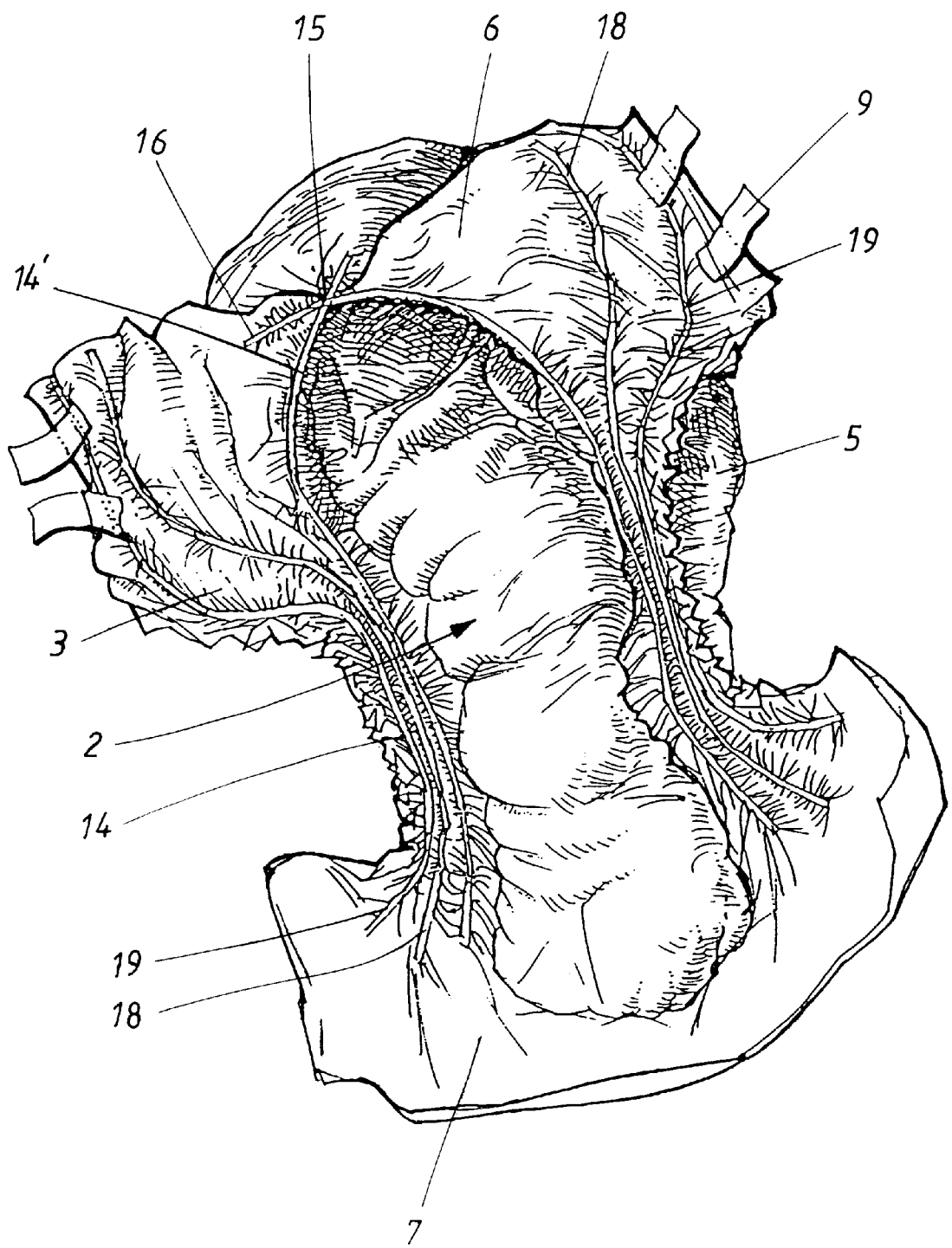
FIG. 2 is a perspective view of the diaper according to FIG. 1, in its use position.

The diaper 1 according to FIGS. 1 and 2 is a so-called all-in-one diaper having an absorbent body 2 enclosed by a cover 3 consisting of a liquid-permeable inner layer 4, intended to face the user when the diaper is in use, and a liquid-impermeable outer layer 5 which is applied on the opposite side of the absorbent body.

The inner layer and the outer layer extend outside the absorbent body 2, around its full circumference, and are there mutually attached for formation of the cover.

The diaper 1 as a whole has an assymetrical, principally hourglass-like shape with a front portion 6, a rear portion 7 and a narrower crotch portion 8.

When the diaper is in use, the front and rear portions are intended to bear on the corresponding portions of the wearer and enclose the wearer's torso while the crotch portion forms leg openings for the user.

Tape members 9 are permanently affixed on the rear portion and have outwardly foldable fastening parts (not shown) which are intended to be connected to the outside of the front portion of the diaper when it is put on. The absorbent body 2 consists of two assymetrical hourglass-like layers, one minor absorbent layer 10 located directly underneath the inner layer and, seen from the inner layer, one lower major absorbent layer 11. The layer 11 extends with one of its end portions 12 into the rear portion 7 of the diaper and has, in the direction towards the end of the diaper, a tapering shape, with a rounded semicircular-like outer edge 13. The lower major layer 11 of the absorbent body may, for example, be constituted of so-called fluff pulp of cellulose with a density of between 0.08–0.30 g/cm$^3$. The upper minor absorbent layer 10 may likewise consist of so-called fluff pulp but with a lower density than that of the lower major layer. The upper absorbent layer has larger pores than the lower layer and has the ability to rapidly transmit large amounts of urine.

The upper, minor absorbent layer may also be constituted of another material, suitably a porous and elastic material with the ability to rapidly recieve liquid. This property should also substantially be retained after wetting of the material. The material should also contribute to low rewetting in order to make the diaper feel dry to the touch after wetting. The porous and elastic material is preferably composed of a polymeric foam material or of a wadding or a nonwoven of synthetic fibres. As an example of a suitable material may be mentioned a composite non-woven fabric material consisting of a first layer of non-woven fabric of synthetic fibres with a basis weight of between 10 and 30 g/m$^2$ and a second layer of a carded wadding of synthetic fibres with a basis weight of between 20–60 g/m$^2$ and which two layers are united by means of needling. Such a material is described in GB Patent Application no. 9323707.1.

The liquid-permeable inner layer 4 may consist of, for example, a non-woven fabric or of a soft, perforated plastic film, for example of polyethylene. The outer layer 5 consists of a liquid-impermeable material, such as a thin film of polyethylene.

The diaper further comprises in said inner and/or outer layers pre-tensionally applied elastic means. These may be constituted of elastic threads, bands, elastic foam or the like.

In the embodiment shown in FIGS. 1 and 2, a first elastic thread, band or the like 14 is applied on both sides of the absorbent body. The first elastic thread forms leg elastic in the crotch region and, in the rear portion 7 of the diaper, follows the rounded edge portion 13 equidistantly from this portion. The first elastic threads 14 on both sides of the absorbent body intersect each other in a point of intersection 15 just in front of the middle of the rounded edge portion. The two intersecting first elastic threads extend further a distance 16 laterally towards the edge portion of the diaper until they reach the rear edge of the cover 17.

In the diaper according to FIGS. 1 and 2, second and third elastic threads 18 and 19, respectively, are included on both sides of the absorbent body. In the crotch region the second and third elastic threads extend essentially parallel to the first thread and thereby reinforce the leg elastic. Outside of the crotch region in the rear portion the second and third threads 18, 19 essentially extend in the longitudinal direction of the diaper.

During the manufacture of the diaper, the elastic threads in the front portion of the diaper are extended along the threads indicated in the drawing with dotted lines, but since elastic material may interfere with the tape function, the elastic threads in the shown embodiment have not been glued along the dotted portions but have been relieved from tension and accordingly been allowed to contract inwards, i.e. elastic is not present along the dotted lines.

As they strive to contract, the first elastic threads 14, in the curved elastic portions 14' in the rear portion of the diaper, exert tensile forces, in FIG. 1 indicated with arrows A, in a direction towards the centre of curvature of the curved portion of the elastic portion 14. The absorbent layer 11 has sufficient bending resistance to make the rounded edge 13 on the absorbent layer serve as a folding notch for the cover when this, along the curved elastic portion 14, is pulled towards the centre of curvature, which in the shown embodiment is located in the vicinity of the rear end of the minor absorbent layer 10.

When the diaper as a whole is curved in connection with being put on the user, the tensile forces A lift the cover up around the rounded edge 13 of the absorbent body to form a leakage barrier which projects vertically above the absorbent body. The distance between the rounded absorbent body and the curved elastic portion may be of the magnitude of 1 cm up to several cm. In the shown embodiment, as is evident from FIG. 2, the complete rear portion of the core will be enclosed by a sealed bowl.

Leakage often occurs across the side and the rear. Arresting a rivulet immediately next to the core causes the urine be re-absorbed instead of finding its way to the edge of the diaper where leakage will occur.

Said bowl, which is formed by the curved elastic portions 14, is of course efficient for the retention of faeces within the bowl.

The elastic portions 16 extending a distance laterally from the point of intersection 15 serve as waist elastic in the shown embodiment.

The first elastic threads 14 accordingly have no less than three functions: they serve as leg elastic, form a leakage-preventing bowl and form leg elastic.

The second and third elastic threads 18, 19 serve as leg elastic in the crotch portion and as additional leakage barriers in the rear portion 7 of the diaper, where the threads pull the cover together along said threads.

Figure 3:
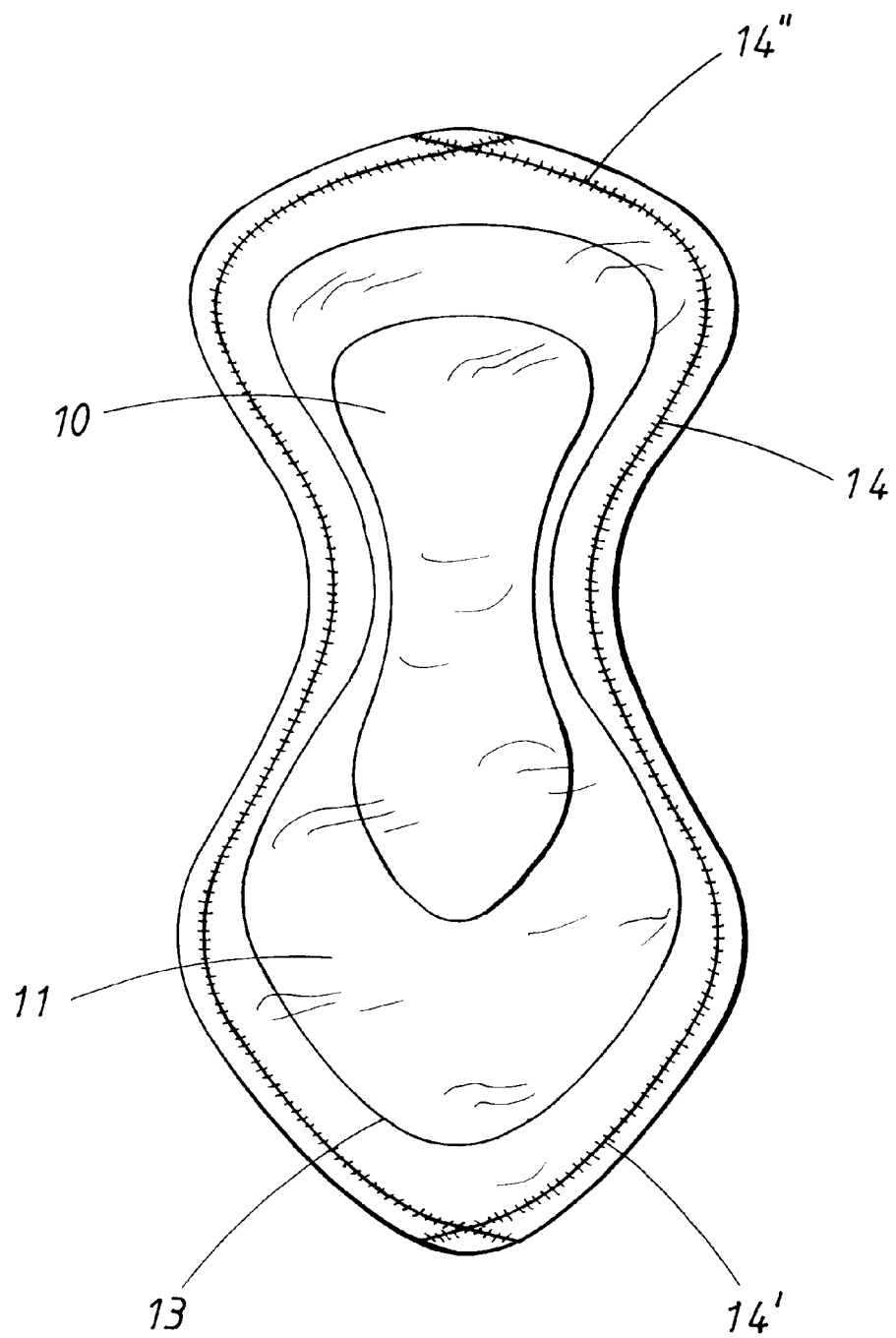
FIG. 3 is a plan view of the article according to the invention in a second embodiment.

In the embodiment shown in FIG. 3, the article is constituted by an insert diaper which is supported and kept in place on the user by a separate pair of pants (not shown).

In the embodiment according to FIG. 3 the details corresponding to the same components have been provided with the same reference numerals.

The absorbent body 2 is identical to the one described in connection with FIGS. 1 and 2. The cover 3 consisting of a liquid-permeable inner layer 4 and a liquid-impermeable outer layer 5, extends principally equidistantly outside the absorbent body around its complete circumference and forms edge portions where the inner and outer layers are joined. Elastic threads 14 extend along the edge portion, the curved portions 14', 14" of which threads form erect leakage barriers above the absorbent body. These barriers form urine- and faeces-receiving bowls when the diaper is in use, i.e. when it is curved.

The invention is not restricted to the embodiments described above but a number of modifications are possible within the scope of the subsequent claims.

The elastic means may be made up of one or several transverse threads which are applied in a curved path around a rounded front portion of the absorbent body for formation of erect leakage barriers at the front of the diaper. Thus, embodiments without leg elastic are conceivable.

The article according to the invention may be constituted by a pair of training pants, i.e. a diaper in the form of pants with waist and leg openings.

Similar constructions of pants which are to serve as sanitary napkins are also conceivable within the scope of the invention.

What is claimed is:

1. Disposable liquid-absorbent article having an elongate shape and comprising:

an absorbent body having a front portion, a rear portion and a thickness;

a cover enclosing said absorbent body;

said cover comprising a liquid-permeable inner layer on the side of the absorbent body facing a user during use and a liquid-impermeable outer layer on the opposite side of the absorbent body, the outer and inner layers being mutually connected outside the absorbent body and comprising one or several pretensionally applied elastic means; and at least one of the front and rear portions of the absorbent body has a longitudinally tapering shape with a rounded outer edge, the elastic means are connected to at least one of the two layers and extend across the article and in a curved path outside the absorbent body along the rounded outer edge and at essentially equal distance from the rounded outer edge, which distance exceeds the thickness of the absorbent body, whereby the elastic means through striving to contract and exert tensile forces across the rounded outer edge in a direction towards the center of curvature of the rounded outer edge and, when in use, thereby lift the cover around the rounded outer edge of the absorbent body for formation of a leakage barrier which projects of an angle with respect to the absorbent body.

2. The article as claimed in claim 1, with a front portion, a rear portion and a narrower crotch portion, which when the article is in use form leg openings, wherein the elastic means of the article are constituted by at least one first elastic thread, band or the like on both sides of the absorbent body, that said threads on both sides of the absorbent body in the crotch portion form leg elastic and at least in either the front or the rear portion follow the rounded end portion for formation of said leakage barrier, whereby the respective elastic threads on both sides of the absorbent body intersect at a point of intersection just in front of the middle of the rounded end portion.

3. The article as claimed in claim 2, wherein said intersecting threads, extend from the point of intersection further at least a distance laterally towards the edge portion of the article in the front and rear portion, respectively, and there form waist elastic.

4. The article as claimed in claim 2, wherein at least a second elastic thread, band or the like is arranged on both sides of the absorbent body, and that said second elastic thread extends in the crotch region essentially parallel to the first elastic thread and thereby reinforces the leg elastic, and that the second elastic thread outside the crotch region at least in either the front or rear portion extends essentially in the longitudinal direction of the article towards its end edge, whereby the other elastic threads in the front and rear portion, respectively, contract the cover and form further barriers along the other threads.

5. The disposable liquid-absorbent article according to claim 1, wherein the leakage barrier projects in a substantially vertical direction with respect to the absorbent body.

* * * * *